United States Patent
Kessler

(10) Patent No.: US 7,584,664 B2
(45) Date of Patent: Sep. 8, 2009

(54) ACOUSTIC MICRO IMAGING DEVICE HAVING AT LEAST ONE BALANCED LINEAR MOTOR ASSEMBLY

(75) Inventor: Lawrence W. Kessler, Buffalo Grove, IL (US)

(73) Assignee: Sonoscan Inc., Elk Grove Village, IL (US)

( * ) Notice: Subject to any disclaimer, the term of this patent is extended or adjusted under 35 U.S.C. 154(b) by 375 days.

(21) Appl. No.: 11/626,177

(22) Filed: Jan. 23, 2007

(65) Prior Publication Data
US 2007/0180914 A1    Aug. 9, 2007

Related U.S. Application Data

(60) Provisional application No. 60/765,917, filed on Feb. 7, 2006.

(51) Int. Cl.
*G01N 29/06* (2006.01)
*G01N 29/265* (2006.01)

(52) U.S. Cl. .............. 73/620; 73/625; 73/633; 73/634

(58) Field of Classification Search .......... 73/633, 73/634
See application file for complete search history.

(56) References Cited

U.S. PATENT DOCUMENTS

| | | | | |
|---|---|---|---|---|
| 2,937,522 | A | * | 5/1960 | McGaughey ............ 73/633 |
| 4,021,771 | A | * | 5/1977 | Collins et al. ............ 367/8 |
| 4,455,872 | A | * | 6/1984 | Kossoff et al. .......... 73/618 |
| 4,518,992 | A |   | 5/1985 | Kessler et al. |
| 4,768,155 | A | * | 8/1988 | Takishita et al. ........ 702/39 |
| 4,781,067 | A | * | 11/1988 | Cichanski ............... 73/620 |
| 4,866,986 | A |   | 9/1989 | Cichanski |
| 4,995,259 | A |   | 2/1991 | Khuri-Yakub et al. |
| 5,600,068 | A |   | 2/1997 | Kessler et al. |
| 5,602,336 | A | * | 2/1997 | Takeuchi et al. ........ 73/624 |
| 5,684,252 | A |   | 11/1997 | Kessler et al. |
| 6,357,136 | B1 |   | 3/2002 | Erickson et al. |
| 6,460,414 | B1 |   | 10/2002 | Erickson |
| 6,641,539 | B2 |   | 11/2003 | Hirooka et al. |
| 6,880,307 | B2 |   | 4/2005 | Schwitte et al. |
| 6,880,387 | B2 |   | 4/2005 | Kessler et al. |
| 6,890,302 | B2 |   | 5/2005 | Oravecz et al. |

(Continued)

OTHER PUBLICATIONS

PCT Written Opinion, International Application No. PCT/US07/061137, dated Jan. 26, 2007 (6 pages).

(Continued)

*Primary Examiner*—Hezron Williams
*Assistant Examiner*—Rose M Miller
(74) *Attorney, Agent, or Firm*—Marshall, Gerstein & Borun LLP

(57) ABSTRACT

A scanning acoustic microscope including an ultrasonic transducer and a balanced linear motor assembly is disclosed. The balanced linear motor assembly includes a counterweight that is mounted for movement along a linear path that is parallel to the first linear path on which the transducer travels. The counterweight has a mass that is generally equal to the mass of the rotor and the transducer. The counterweight is being adapted to be moved, when the scanning acoustic microscope is used to interrogate a sample, along the second linear path at the same time that the rotor and transducer are being moved along the first linear path to allow the transducer to accelerate and decelerate without creating vibration.

22 Claims, 7 Drawing Sheets

U.S. PATENT DOCUMENTS

| | | |
|---|---|---|
| 6,895,820 B2 | 5/2005 | Oravecz et al. |
| 6,981,417 B1 | 1/2006 | Oravecz |
| 7,258,668 B2 | 8/2007 | Hirooka et al. |
| 2003/0045768 A1 | 3/2003 | Hirooka et al. |
| 2004/0048111 A1 | 3/2004 | Halme et al. |
| 2004/0173024 A1 | 9/2004 | McKeon |
| 2005/0116188 A1 | 6/2005 | Yagi |
| 2005/0160818 A1 | 7/2005 | Mueller |
| 2005/0233437 A1 | 10/2005 | Kureshy et al. |
| 2006/0100529 A1 | 5/2006 | Rueckmann et al. |
| 2007/0012115 A1 | 1/2007 | Busch et al. |
| 2009/0095086 A1* | 4/2009 | Kessler et al. ......... 73/606 |

OTHER PUBLICATIONS

PCT International Search Report, PCT/US04/10911, dated Feb. 16, 2005 (4 pages).

* cited by examiner

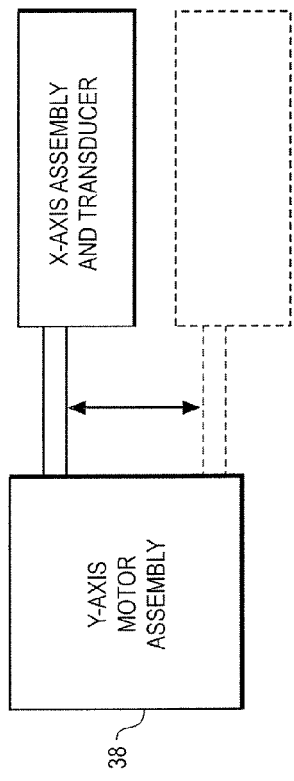
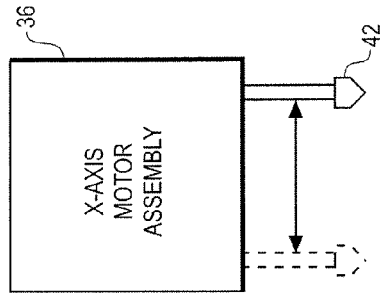
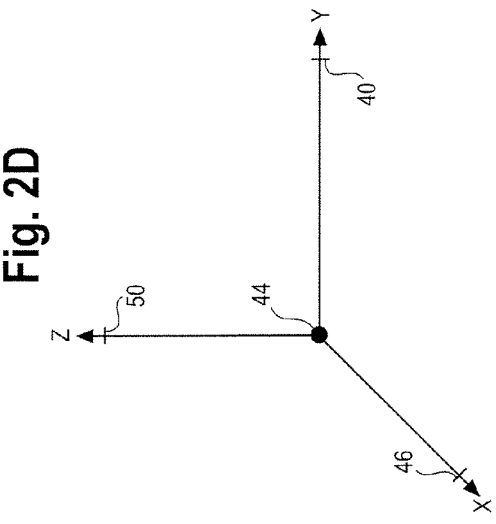
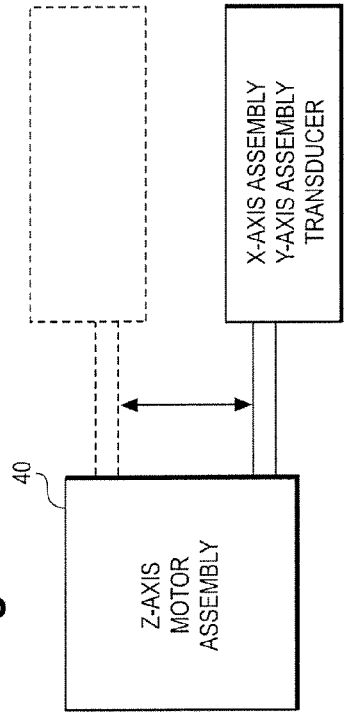

US 7,584,664 B2

ACOUSTIC MICRO IMAGING DEVICE HAVING AT LEAST ONE BALANCED LINEAR MOTOR ASSEMBLY

CROSS-REFERENCE TO RELATED APPLICATIONS

This application claims the benefit of provisional application Ser. No. 60/765,917, filed Feb. 7, 2006, the content of which is incorporated by reference into this application as if fully set forth herein.

BACKGROUND OF THE INVENTION

The present invention generally relates to improvements in the field of non-destructive testing and failure analysis using pulsed ultrasonic energy. More particularly, the present invention concerns a device for performing acoustic micro imaging ("AMI") operations that utilizes a balanced linear motor to move an acoustic transducer in at least one direction.

Various issued patents disclose AMI devices that utilize pulsed ultrasonic energy for purposes of non-destructive testing and failure analysis. For example, U.S. Pat. No. 4,781,067 discloses a balanced scanning mechanism. In the abstract of this patent, it is stated that the mechanism disclosed in the patent is used to drive a transducer of an acoustic microscope or other instrument rapidly back and forth along a linear path comprising the X portion of an X-Y scan pattern. The abstract also states that the transducer is mounted on a first carriage, and that a counterweight may be mounted on a second carriage, with the total mass of each carriage and the contents thereon being equal. The abstract further states that drive belts are connected to both carriages to drive them reciprocally along the X axis with accelerations and velocities that are equal in amplitude but opposite in direction. Conventional motors and pulleys are used to drive the belts. The content of this patent is incorporated by reference into this application as if fully set forth herein.

As another example, U.S. Pat. No. 6,357,136 issued on Mar. 19, 2002, and is entitled scanning acoustic microscope system and method for handling small parts. The abstract of this patent states that the use of the invention prevents the dislodging of small, loosely held parts from trays during inspection or during drying. The content of this patent is incorporated by reference into this application as if fully set forth herein.

A further example is U.S. Pat. No. 6,880,387, which issued on Apr. 19, 2005, and which is entitled acoustic micro imaging method providing improved information derivation and visualization. The abstract of this patent states that an acoustic image of a sample is derived, and then visual superposition of one or more additional images is obtained. The content of this patent is incorporated by reference into this application as if fully set forth herein.

A still further example is U.S. Pat. No. 6,890,302, which issued on May 10, 2005, and which is entitled frequency domain processing of scanning acoustic micro imaging signals. In the abstract of this patent, it is stated that a time domain signal, which is representative of acoustic impedance features in a sample, is obtained, and then is converted to the frequency domain. The abstract also states that the frequency domain signal can be modified, and then converted back to a time domain signal. The content of this patent is incorporated by reference into this application as if fully set forth herein.

An additional example is U.S. Pat. No. 6,895,820, which issued on May 24, 2005, and which discloses an acoustic micro imaging method and apparatus for capturing 4D acoustic reflection signals. The abstract of the patent states that an ultrasonic transducer is utilized to interrogate a sample at three dimensionally varied locations within the sample, with an in-focus A-scan being produced for each location interrogated. The content of this patent is incorporated by reference into this application as if fully set forth herein.

A further example is U.S. Pat. No. 6,981,417, which issued on Jan. 3, 2006, and which discloses a scanning acoustic micro imaging method and apparatus for non-rectangularly bounded fields. The abstract of this patent states that a stage system is commanded so that an ultrasonic probe interrogates a non-rectangularly bounded space on the sample surface and/or within the volume of the sample. The patent also states that FIGS. 21-29 schematically illustrate various 2D and 3D scanning modes and techniques which may be employed in connection with the invention disclosed in the patent. The content of this patent is incorporated by reference into this application as if fully set forth herein.

Other patents that disclose various AMI devices include U.S. Pat. Nos. 6,460,414, 5,684,252, 5,600,068, 4,866,986 and 4,518,992. The content of these patents are incorporated by reference into this application as if fully set forth herein.

A number of published patent applications disclose various other AMI devices. For example, US Published Patent Application Nos. 20030045768 and 20040048111 are entitled "ultrasonic probe for operation under microscope." Paragraph 169 of both publications state that "an advancing/withdrawing mechanism" for a "reflector 61" may be constructed with "a linear motor 62 and a switch 63." The content of these publications is incorporated by reference into this application as if fully set forth herein.

As an additional example, U.S. Patent Publication No. 20040173024 is entitled "method and apparatus for temperature controlled ultrasonic inspection." This publication states that the "relative positions of the object under inspection 130 and the ultrasonic transducer 102 are adjusted along a scan-line by action of a first position controller 134 (such as linear-motor or a stepper-motor under control of the system computer 106) that moves the transducer along a track 136." The content of this publication is incorporated by reference into this application as if fully set forth herein.

In August of 2001, a company called Sonix issued a press release which describes its scanning acoustic microscope model no. UHR-2001. The press release states that the UHR-2100 microscope includes a 0.5 micron encoder on the scan axis, an improved ball screw for greater positioning accuracy, a linear servo motor, and a transducer that is directly coupled to a servo forcer.

Currently available AMI devices having a linear motor, such as those described above, are significantly limited in use. In order for useful data to be obtained in an AMI operation, vibration that is caused when the transducer assembly is accelerated or decelerated must be kept below a certain ceiling amount. For example, the linear motors used in the above-referenced devices must be subject to not more than 0.1 G when accelerated or decelerated. As a result of this, the linear motors can be operated at top speed only about no more than 40% of the time. When the linear motors are operated at such low efficiencies, the time that is required to scan a particular sample (e.g., an integrated circuit package) is necessarily substantially increased well beyond what would be possible if the motor were operated at a higher efficiency rating. This disadvantage is compounded when the AMI device is used to perform failure analyses on trays of samples in commercial applications, which leads to an undesirable increase in costs.

BRIEF DESCRIPTION OF THE DRAWINGS

Various examples objects, features and attendant advantages of the present invention will become fully appreciated as the same becomes better understood when considered in conjunction with the accompanying drawings, in which like reference characters designate the same or similar parts throughout the several views, and wherein:

FIG. 2A-2C are general, schematic diagrams which illustrate a first embodiment of the present invention that includes three separate balanced linear motor assemblies that are used to drive an ultrasonic transducer in the X, Y and Z directions;

FIG. 2D is a drawing which illustrates the space in which the ultrasonic transducer shown in FIGS. 2A-2C can be moved from an initial position to an outer limit in each of the X, Y and Z directions;

DETAILED DESCRIPTION OF THE PREFERRED EMBODIMENTS

Figure 1:
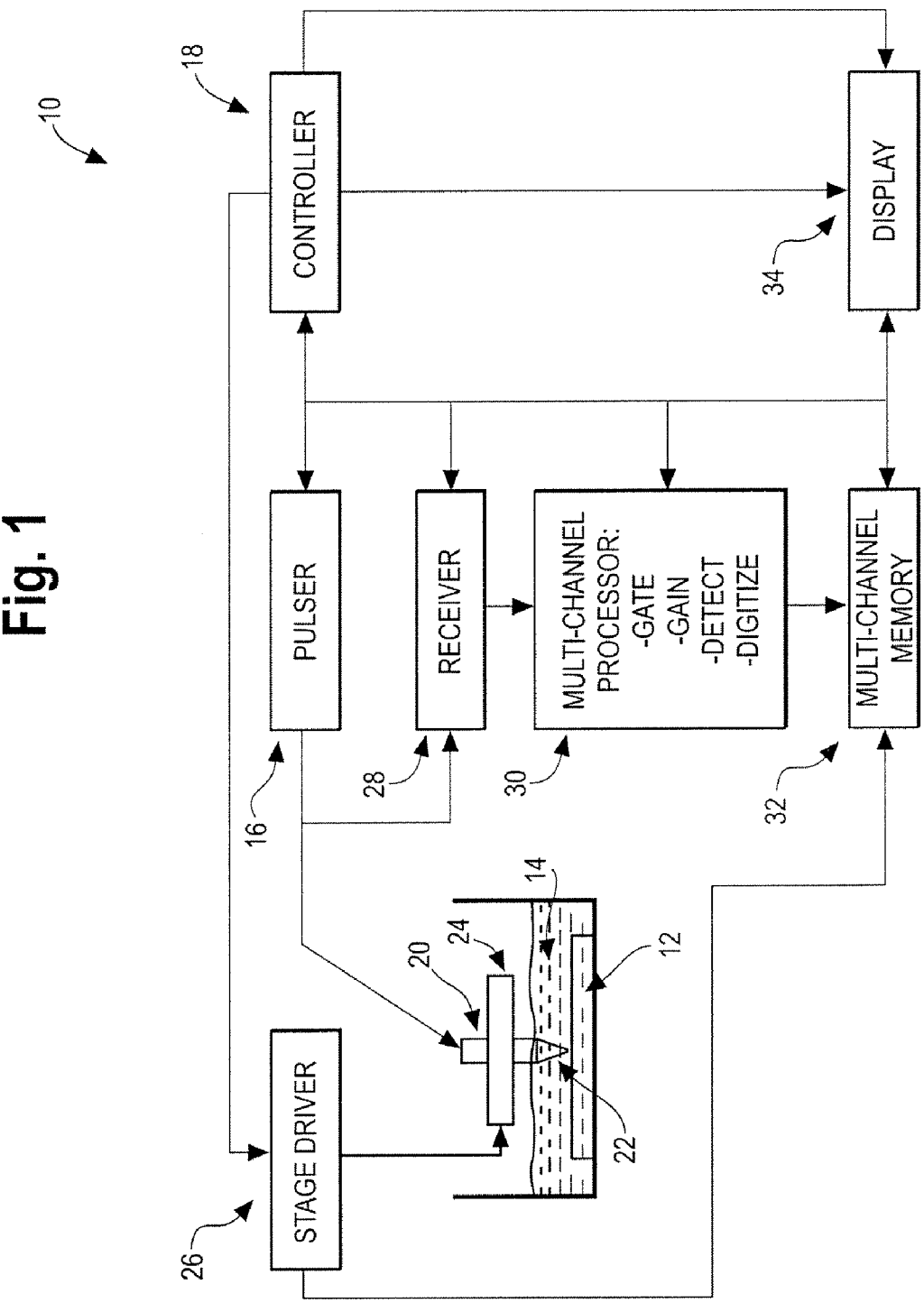
FIG. 1 is a schematic drawing which shows a scanning acoustic microscope that incorporates aspects of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description Of The Invention", relates to a requirement of the United States Patent Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

Referring to FIG. 1, a schematic drawing of a scanning acoustic microscope 10 that incorporates aspects of the present invention is illustrated. Microscope 10, as shown in FIG. 1, is adapted to inspect a sample 12 (e.g. an integrated circuit package) that is submerged in a coupling medium 14. Sample 12 can be inspected by itself as is the case, for example, in laboratory applications, or can be, for example, mounted on a tray of other parts to be inspected, which typically is the case in commercial applications.

A pulser 16 is under the control of motion controller 18 and is used to excite a transducer 20 to generate pulses of ultrasonic energy, typically at frequencies ranging from 10 MHz or lower to 230 MHz or higher. One pulse of ultrasonic energy 22 is shown in FIG. 1. The transducer 20 is scanned in X, Y and Z coordinates by an X-Y-Z stage 24 through an X-Y-Z driver 26, which is under the control of controller 18. The controller includes, for example, a set of instructions stored in memory that cause the transducer 20 to be moved in a desired patent with respect to a sample that is to be inspected.

The transducer 20 is adapted to receive reflections of the ultrasonic pulses that are directed towards and then reflected by acoustic impedance features present in the sample 12. Such reflection signals are processed by a receiver 28 in analog form, and are supplied to a multi-channel processor 30. Digitized versions of the reflection signals can be stored in multi channel memory 32, and, if desired, shown on display 34. In a particular embodiment of the present invention, multi channel memory 32 will store, for example, an in-focus A-scan of a plurality of three dimensionally varied points on the surface of or within the interior of the sample 12.

FIGS. 2A-2C are general, schematic diagrams which illustrate a first embodiment of the present invention that includes three separate balanced linear motor assemblies 36, 38 and 40 that are used to move an ultrasonic transducer 42 in the X, Y and Z directions. In FIG. 2D, the initial, at-rest position of ultrasonic transducer 42 is shown as location 44. Linear motor assembly 36 is used to drive the ultrasonic transducer 42 from the initial location 44 to an outer limit 46 along the X axis. Linear motor assembly 38 drives the X axis motor assembly 36 and the transducer 42 so that the transducer can be moved along the Y axis from initial location 44 to an outer limit. Similarly, linear motor assembly 40 is used to drive the X axis motor assembly 36, the Y axis motor assembly 38 and the ultrasonic transducer 42 along the Z axis so that the transducer can be moved along the Z axis from initial location 44 to outer limit 50.

In one embodiment of the present invention, the Y motor assembly includes two balanced linear motor assemblies (hereinafter described) that are attached, for example, to distal ends of the X axis motor assembly which supports the transducer. In another embodiment, the Z axis motor assembly comprises three balanced linear motor assemblies that are attached to complementary portions of the Y axis motor assembly. It should be understood, however, that any configuration of balanced linear motor assemblies can be used to accomplish purposes of the present invention.

By using a separate balanced linear motor assembly to control the path of movement of the transducer 42 with respect to the sample 12, it is possible for the transducer to move very quickly in any direction within the sample (e.g., a helical pattern), not just in a standard X-Y raster scan. One advantage is that, for example, non-rectangularly bounded areas on the surface of or within the space of, for example, hermetically sealed packages of medical instruments can be quickly inspected by causing the transducer to follow a desired path throughout the space or volume to be scanned.

In applications where speed in the Z direction is not critically important, it is possible to use a balanced linear motor assembly to drive the transducer 42 in the X and Y directions, with a conventional motor assembly being used to control transducer movement in the Z direction. Similarly, in applications where it is important to quickly move in one direction (e.g., an elongated rectangular scan), it is possible to use a balanced linear motor assembly to control movement in the X direction, with movement in the Y and Z directions being controlled by conventional motor assemblies because incremental movement in those directions is small in such applications.

Figure 3:
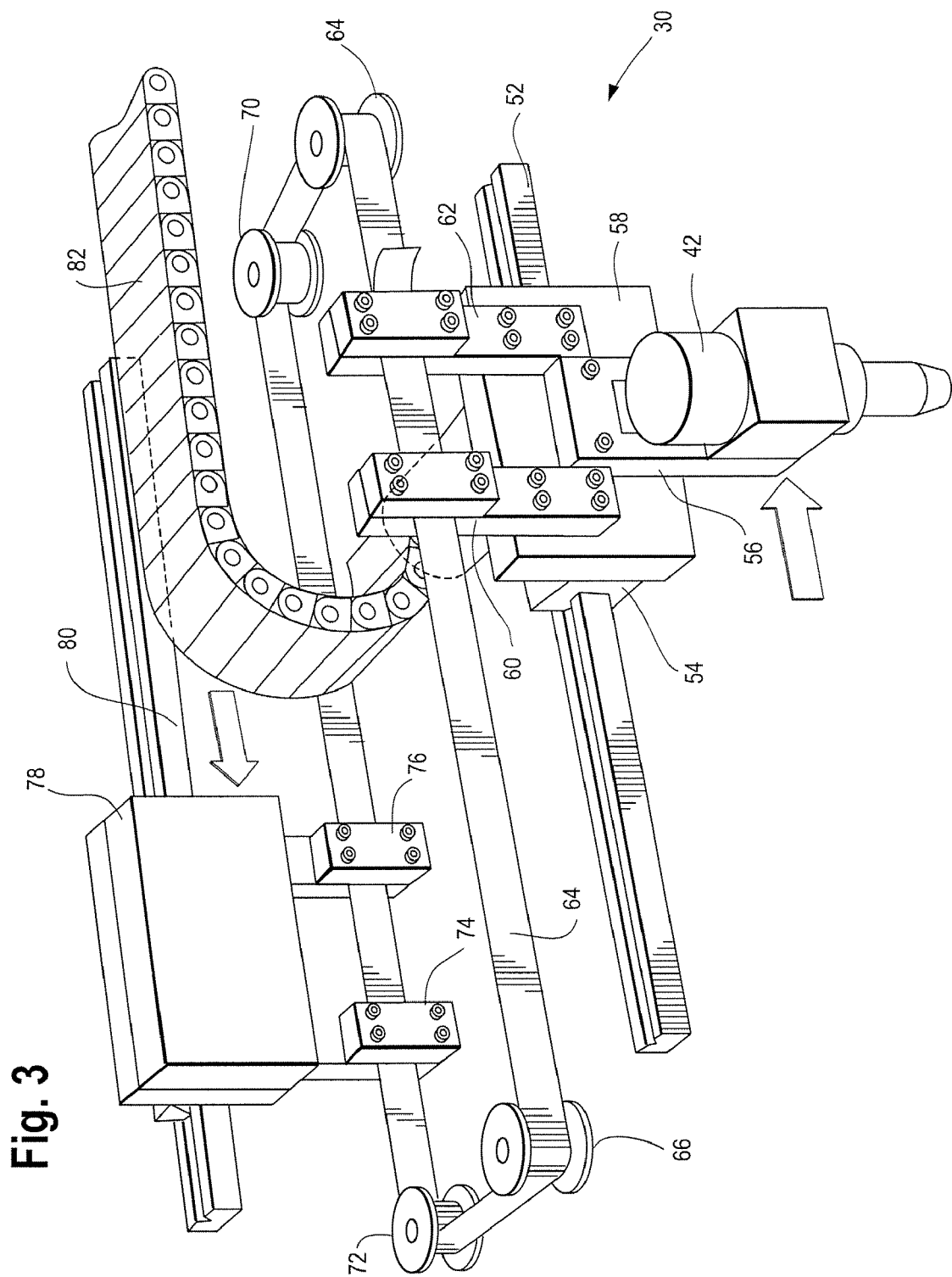
FIGS. 3 and 3A-3B are perspective views of a balanced linear motor assembly that is used to move an ultrasonic transducer along the X axis.
Figure 3A:
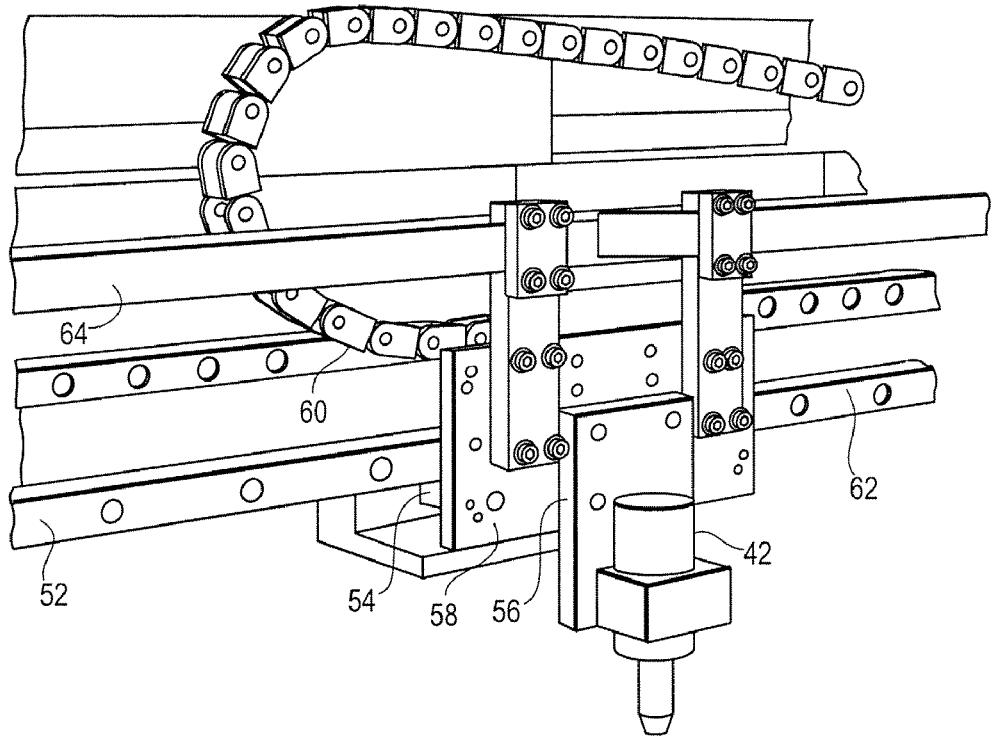
Figure 3B:
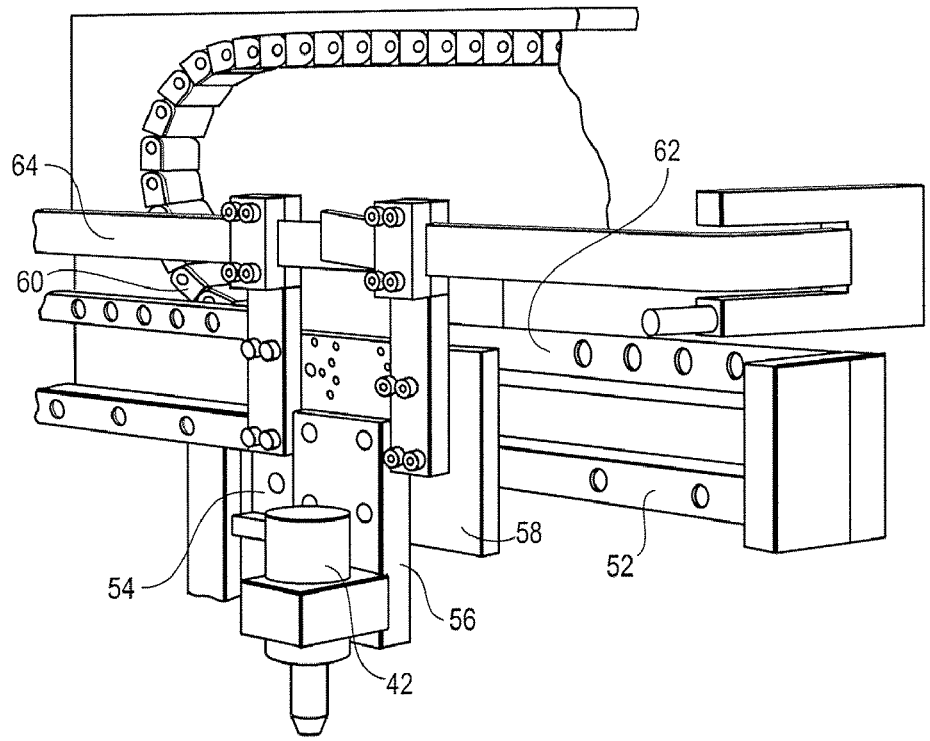

FIGS. 3 and 3A-3B are perspective views of linear motor assembly 36 shown in FIG. 2A. Assembly 36 includes a linear motor stator 52 and a linear motor rotor 54 that is slidably mounted thereon. As is readily apparent to those of ordinary skill in the relevant art, the application of electric current to rotor 54 causes it to move along the axis defined by stator 52. Position sensors (not shown) are included to allow the controller 18 (FIG. 1) to be aware of the position of rotor 54 with respect to stator 52. Linear motors, linear bearings and other equipment suitable for use in connection with the present invention are commercially available and described at www.trilogysystems.com. Such motors include, for example, ironless linear motors, and linear motors with cogging torque reduction capabilities, and which are capable of attaining top speeds of, for example, 1 meter per second. Such motors are, for example, capable of subjecting a transducer assembly up to, for example, 10 G of force during acceleration or deceleration.

In designing a balanced linear motor assembly in accordance with the present invention, an important criteria to keep in mind is the life of the linear motor. The current flow in a linear motor is quite high when the motors are accelerated or decelerated with too much force. Thus, one may utilize a linear motor that subjects the transducer assembly to about 5 G of force, which causes a low enough amount of current during operation to not deleteriously effect the life of the motor.

Figure 3C:
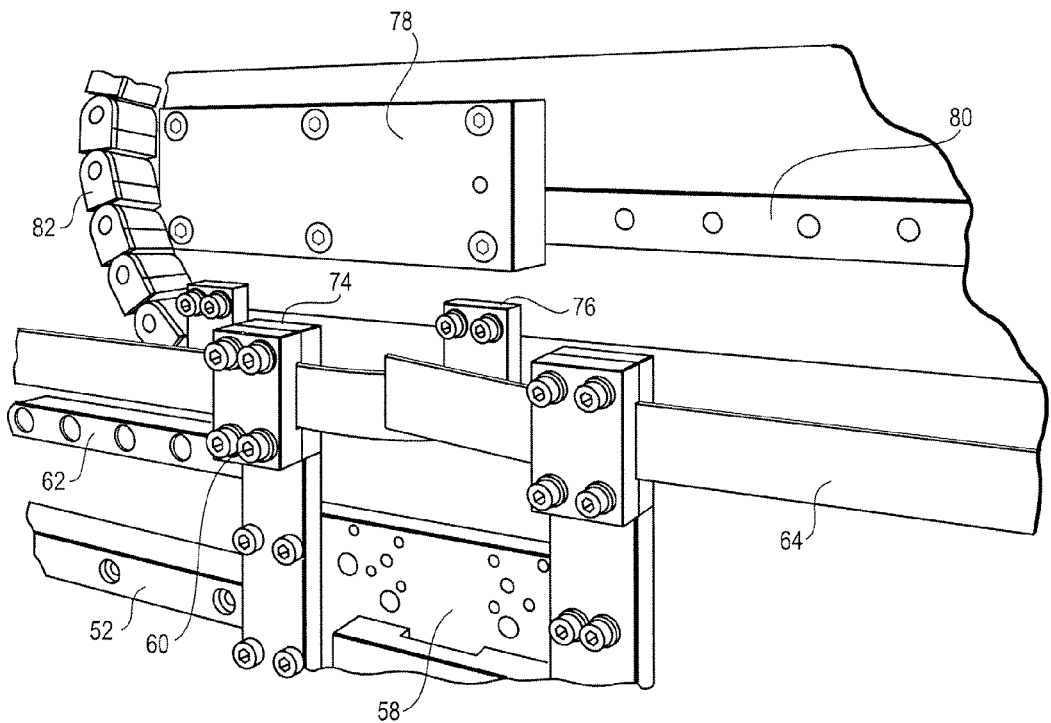
FIGS. 3C and 3D are close-up views of a portion of the balanced linear motor assembly that is shown in FIGS. 3-3B.
Figure 3D:
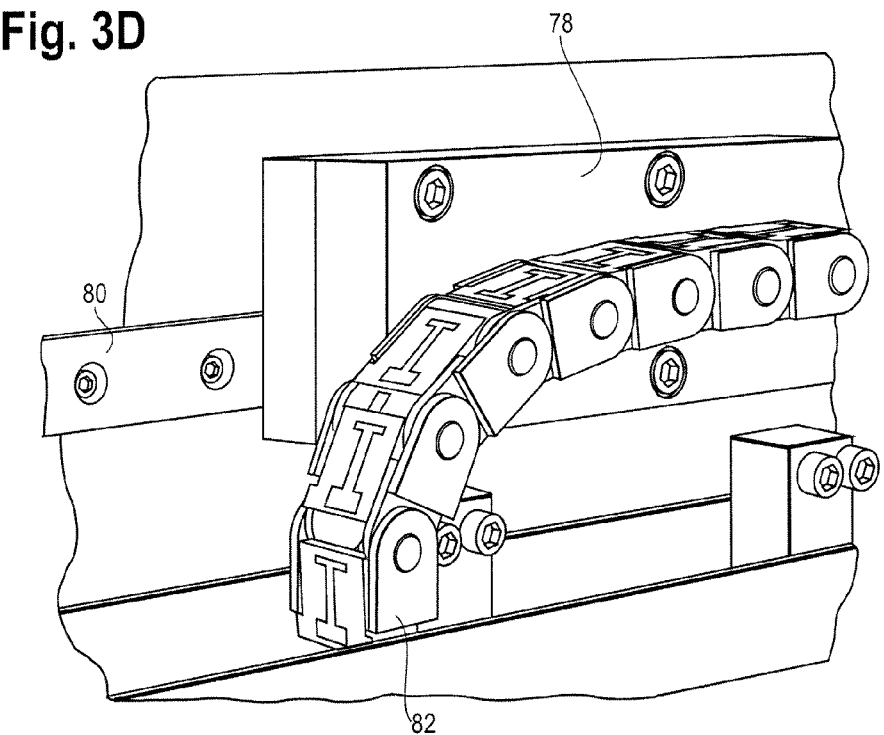

Transducer 42 is mounted on a support bracket 56 that is secured to rotor 54 via mounting plate 58. Two connectors 60 and 62 are used to connect the mounting plate 58 to a belt 64. Belts 64 is moved about and contacts pulleys 66, 68, 70 and 72. Belt 64 also is secured to connectors 74 and 76, which support a counterweight 78 for movement along linear bearing 80. Flexible support member 82 is included so that appropriate electrical connections (not shown) can be made to the transducer 42, to the rotor 54 and to the position sensors (not shown) which are used to sense the position of the rotor with respect to the stator. The position sensor information is fed back to control 18 (FIG. 1). FIGS. 3C and 3D are close-up views of a portion of the balanced linear motor assembly 36 shown in FIGS. 3-3B.

In accordance with the embodiment shown in FIGS. 3-3D, the belt 64 causes the counterweight 78 to move in a direction that is opposite to the direction in which the transducer is moved. In accordance with the present invention, the total mass of the counterweight 78 and connectors 74 and 76 is generally equal to the total mass of the rotor 54, mounting plate 58, support bracket 56 and connectors 60 and 62. In a preferred embodiment, the total masses are equal to each other. By doing this, the force that is generated when the transducer 42 is accelerated or decelerated is balanced by the force that is generated by the acceleration or deceleration of the counterweight 78. Because both total masses are moved in opposition directions, the forces generated cancel each other. This allows, for example, the transducer 42 to be quickly accelerated or decelerated with, for example, 5 G of force and, therefore, allows efficiently scanning operations to be performed at much higher rates than that which is possible with conventional AMI devices.

To further improve the operation and accuracy of the operation of AMI device 10, it is possible to design the counterweight 78 so that its center of mass is as close as possible to the transducer 42 in the Y direction. By doing so, the rotational force that is created by the opposite movement of the counterweight 78 and the transducer 42 is minimized. This effect can be even further enhanced by designing the support structure that mounts the transducer 42 on the linear motor rotor 54 so that the center of mass of the resulting assembly is located as close as possible to the center of mass of the counterweight 78.

An AMI device that includes a balanced linear motor described in the preceding paragraphs and that utilizes conventional motors for causing movement along the Y and Z axes can be used in accordance with the teachings of the present invention. Use of such an AMI device provides significant advantages with regard to improving scan times for a given scan area with respect to the time that it would take conventional devices to perform the same scan.

To avoid causing vibrations that would ruin the scan data, the transducers used in prior art devices are subject to an upper limit of acceleration of, for example, a fraction of a G force. Thus, the conventional non-balanced linear motors used in conventional devices are able to run at top scanning speed for a limited amount of time due, for example, to the significantly increased amount of time that it takes for the prior art transducers to repeatedly change directions. Due to the fact that the present invention incorporates, for example, the counterweight 78 which balances the force generated by the movement of the transducer, a scanner manufactured in accordance with the present invention can be deaccelerated and accelerated much more quickly that prior art transducers and, therefore, move at the top scanning speed (e.g., 40 in/sec) for about 90% of the time for a certain scanning application.

Figure 4A:
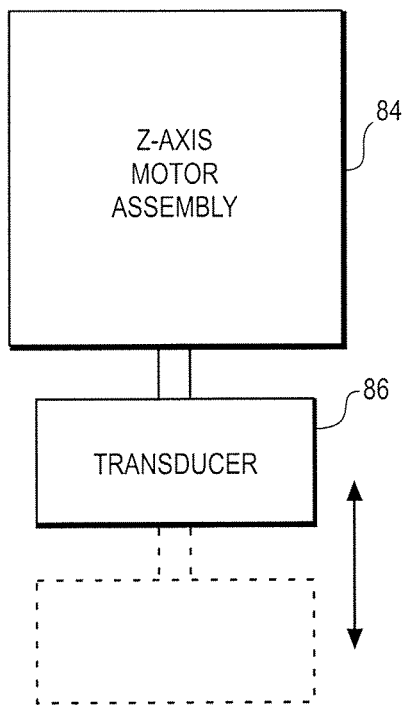
FIGS. 4A-4C illustrate a second embodiment of the present invention, in which separate balanced linear motor assemblies are used to control the movement of an ultrasonic transducer in the X and Y directions, with a conventional stepper motor assembly being used to control transducer movement in the Z direction.
Figure 4B:
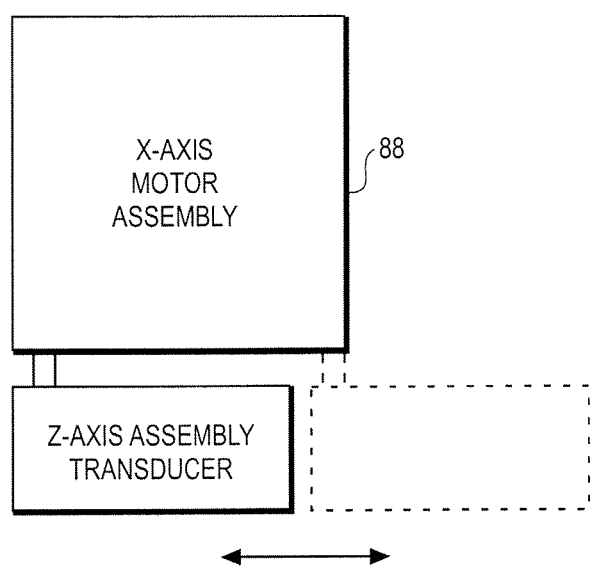
Figure 4C:
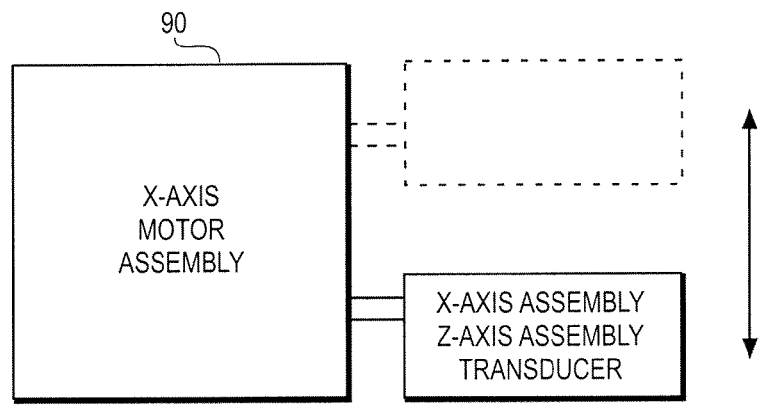

FIGS. 4A-4C illustrate a second embodiment of the present invention. In accordance with this embodiment, a conventional stepper motor or the like 84 is utilized to move a transducer 86 along the Z axis, and a balanced linear motor 88 (as shown, for example, in FIG. 3) is utilized to move the transducer and the Z axis motor 84 along the X axis that is defined by the stator of the linear motor (not shown). In one specific embodiment, the conventional motor 84 is mounted on plate 58 (FIG. 3) so that it can move support bracket 56 up and down along the Z axis. In accordance with this embodiment, a separate balanced linear motor assembly 90 is used to move the X axis motor assembly 88, Z axis motor assembly 84 and transducer 86 about the Y axis.

Figure 5:
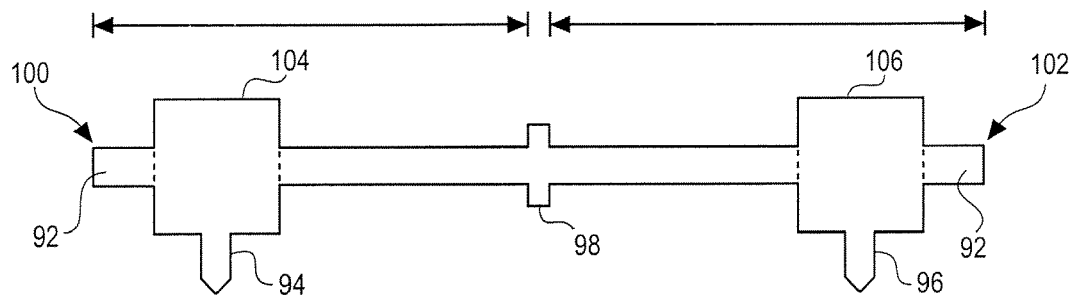
FIG. 5 is a general, schematic diagram of an embodiment of the present invention, in which two ultrasonic transducers are mounted on the stator of a linear motor for movement in opposite directions along the X axis defined by the linear motor stator.

Referring to FIG. 5, a high level, general schematic diagram of a further embodiment of the present invention is shown. In this embodiment, an additional transducer, and not a counterweight, is utilized to generate a compensating force that cancels out the force generated when the first transducer is accelerated or decelerated. In this embodiment, two transducers 94 and 96 are mounted for movement along a linear motor stator 92 between midpoint 98 and ends 100 and 102. Transducers 94 and 96 are operatively coupled to distinct linear motor rotors 104 and 106. The rotors 104 and 106 are caused to move in opposite directions along the stator 102 by, for example, feeding control currents to the rotors 104 and 106 that are of opposite polarity.

By making the total mass of the transducer 94 and rotor 104 be equal to the total mass of the transducer 96 and rotor 106, the forces generated by their movement in opposite directions cancel each other. This allows, for example, scanning operations to be performed much more quickly than is possible in connection with prior art AMI devices. This also allows, for example, the scanning capacity of the present invention to be doubled over what is possible in accordance with the embodiments of the present invention that utilize one transducer. In accordance with this further embodiment, the transducers 94 and 96 are mounted in operative relation to two trays of parts to be inspected (not shown).

Figure 6:
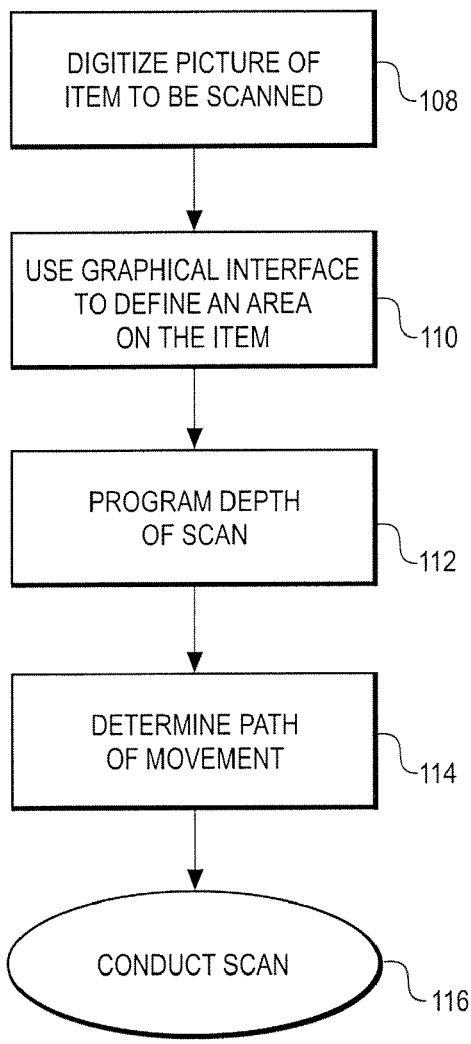
FIG. 6 is a general flowchart that illustrates how a graphical interface can be used to define the path of movement of an ultrasonic transducer to allow the scan of a sample to take place.

FIG. 6 is a general flowchart that illustrates how a graphical interface can be used to define the path of movement of an ultrasonic transducer to allow the scan of a sample to take place. In step 108, a picture of an article to be scanned is digitized and fed into the control system of the inventive AMI device. In step 110, a standard graphical interface is utilized to define a user selected area on the digitized picture of the article to be scanned. This allows a user to define a specific area on the article that is to be scanned. In step 112, a further graphical interface is used to identify varying depths of scan for selected areas on the article to be scanned. In step 114, an algorithm is used to determine the most efficient path of movement of the transducer with respect to the article to be scanned so that the scan is performed in a minimal amount of time. In step 116, the scan is then performed.

A scanning acoustic microscope, comprising an ultrasonic transducer, a balanced linear motor assembly including a rotor on which the transducer is mounted, a stator on which the rotor and transducer are mounted for movement along a first linear path defined by the stator, and a counterweight that is mounted for movement along a second linear path that is parallel to the first linear path, the counterweight having a mass that is generally equal to the mass of the rotor and the transducer; a controller that is electrically connected to the transducer and the balanced linear motor assembly, the controller being adapted to cause the rotor and transducer to be moved along the first linear path in a predetermined sequence of movements to at least partially interrogate a sample; and the counterweight being adapted to be moved, when the sample is being interrogated, along the second linear path at the same time that the rotor and transducer are being moved along the first linear path.

In one embodiment, the transducer follows one or more non-linear traces when the sample is being interrogated.

In another embodiment, the transducer is operatively coupled to the sample via a coupling medium when the sample is being interrogated, the controller being adapted to cause the ultrasonic transducer to emit a pulse of acoustic energy toward each one of a plurality of three-dimensionally varied points located within a given volume defined inside of the sample, the transducer having, for each one of the pulses, a focal point that is disposed at the same location within the given volume of the sample as the corresponding one of the three dimensionally varied points.

In another embodiment, the transducer is operatively coupled to the sample via a coupling medium when the sample is being interrogated, the controller being adapted to cause the ultrasonic transducer to emit a pulse of acoustic energy toward each one of a plurality of three-dimensionally varied points located within a given volume defined inside of the sample, the transducer having, for each one of the pulses, a focal point that is disposed at the same location within the given volume of the sample as the corresponding one of the three dimensionally varied points, the controller being further adapted to cause the transducer to receive a reflection signal corresponding to each one of the pulses, each one of the reflection signals comprising an A-Scan of the sample that is in-focus at the point within the given volume of the sample corresponding thereto, all of the reflection signals representing acoustic impedance features present within the given volume defined inside of the sample.

A scanning acoustic microscope in accordance with the present invention can include, for example, a second motor assembly (e.g., a linear motor assembly or a balanced linear motor assembly) for moving at least the transducer in a direction that is perpendicular to the first linear path.

In accordance with an exemplary embodiment of the present invention, a scanning acoustic microscope can include first and second linear paths, wherein the first linear path is co-linear with the second linear path. The counterweight can be formed, for example, by a second ultrasonic transducer.

The transducer can be returned to a selected speed of the balanced linear motor assembly when changing directions without inducing vibration.

A scanning acoustic microscope in accordance with the present invention can be used to interrogate, for example, a microelectronic sample, a sealed package, or biological material.

A belt and pulley assembly can be used to connect the counterweight to the transducer and rotor.

The controller of a scanning acoustic microscope can cause the transducer to be moved in an X-Y raster scan with respect to a sample.

In an exemplary scanning acoustic microscope, the first and second linear paths can be spaced apart from each other, the center of the mass of the counterweight being located to reduce at least some of the rotational forces that are generated when the transducer is slowed down and changes direction.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed:

1. A scanning acoustic microscope, comprising:
   a balanced brushless linear motor assembly including a stator and a rotor, wherein application of electric current to the rotor causes the rotor to move along a linear path defined by the stator;
   wherein the stator includes at least one permanent magnetic member as a part thereof and the rotor includes at least one winding as a part thereof;
   an ultrasonic transducer that is designed to emit pulses of acoustic energy through a coupling medium and that is directly driven by the rotor;
   a controller that is designed to
   (a) cause control currents to be applied to the at least one winding of the rotor, the flow of the control currents through the at least one winding generating a magnetic field that interacts with a magnetic field emitted from the at least one permanent magnetic member to thereby cause the rotor and ultrasonic transducer to move along the linear path, and
   (b) cause the ultrasonic transducer to emit pulses of ultrasonic energy at a target at predetermined times to at least partially interrogate a target;
   a counterweight that is mounted for movement along a second linear path that is generally parallel to the linear path, the counterweight having generally the same mass as a mass of the ultrasonic transducer and the rotor; and wherein the scanning acoustic microscope is designed so that, whenever the controller causes the rotor and ultrasonic transducer to move in a given direction along the first linear path, the counterweight is moved in the opposite direction along the second linear path thereby allowing the rotor and ultrasonic transducer to be subject to at least five G of force when accelerated or decelerated while maintaining the viability of data that is generated when the target is interrogated.

2. The scanning acoustic microscope of claim 1, wherein the transducer follows one or more non-linear traces when the target is being interrogated.

3. The scanning acoustic microscope of claim 1, wherein the transducer is operatively coupled to the target via a coupling medium when the target is being interrogated, the controller being adapted to cause the ultrasonic transducer to emit a pulse of acoustic energy toward each one of a plurality of three-dimensionally varied points located within a given volume defined inside of the target, the ultrasonic transducer having, for each one of the pulses, a focal point that is disposed at the same location within the given volume of the target as the corresponding one of the three dimensionally varied points.

4. The scanning acoustic microscope of claim 1, wherein the transducer is operatively coupled to the target via a coupling medium when the target is being interrogated, the controller being adapted to cause the ultrasonic transducer to emit a pulse of acoustic energy toward each one of a plurality of three-dimensionally varied points located within a given volume defined inside of the target, the transducer having, for each one of the pulses, a focal point that is disposed at the same location within the given volume of the target as the corresponding one of the three dimensionally varied points, the controller being further adapted to cause the transducer to receive a reflection signal corresponding to each one of the pulses, each one of the reflection signals comprising an A-Scan of the target that is in-focus at the point within the given volume of the target corresponding thereto, all of the reflection signals representing acoustic impedance features present within the given volume defined inside of the target.

5. The scanning acoustic microscope of claim 1, further comprising a second linear motor assembly for moving at least the transducer in a direction that is perpendicular to the linear axis.

6. The scanning acoustic microscope of claim 1, further comprising a second balanced motor assembly for moving at least the transducer in a direction that is perpendicular to the linear axis.

7. The scanning acoustic microscope of claim 1, wherein the first linear path is co-linear with the second linear path.

8. The scanning acoustic microscope of claim 1, wherein the counterweight comprises a second ultrasonic transducer.

9. The scanning acoustic microscope of claim 1, wherein the target comprises a microelectronic target.

10. The scanning acoustic microscope of claim 1, further comprising a belt and pulley assembly that connects the counterweight to the transducer and rotor.

11. The scanning acoustic microscope of claim 1, wherein controller is adapted to cause the transducer to be moved in an X-Y raster scan with respect to the target.

12. The scanning acoustic microscope of claim 1, wherein the first and second linear paths are spaced apart from each other, the center of the mass of the counterweight being located to reduce at least some of the rotational forces that are generated when the transducer is slowed down and changes direction.

13. The scanning acoustic microscope of claim 1, wherein the target comprises a sealed package.

14. The scanning acoustic microscope of claim 1, wherein the target comprises a biological material.

15. A scanning acoustic microscope, comprising:
first and second balanced brushless linear motor assemblies including first and second stators and first and second rotors, respectively, wherein application of current to the first and second rotors causes the first and second rotors to move along first and second linear paths defined by the first and second stators, respectively;
wherein the first and second stators include at least one permanent magnetic member as a part thereof and the first and second rotors include at least one winding as a part thereof;
first and second ultrasonic transducers that are directly driven by the first and second rotors, respectively, and that are designed to emit pulses of acoustic energy through a coupling medium;
a controller that is designed to
(a) cause control currents to be applied to the at least one winding of the first and second rotors, the flow of the control currents through the at least one windings of the first and second rotors generating first and second magnetic fields that interact with first and second magnetic fields emitted from the at least one permanent magnetic members of the first and second stators, respectively, to thereby cause the first and second rotors and the first and second ultrasonic transducers to move along the first and second linear paths, respectively, and
(b) cause the first and second ultrasonic transducers to emit pulses of ultrasonic energy at the target at predetermined times to at least partially interrogate first and second targets;
wherein the first and second linear paths are generally parallel to each other and a mass of the first ultrasonic transducer and the first rotor is generally equal to a mass of the second ultrasonic transducer and the second rotor; and
wherein the scanning acoustic microscope is designed so that, whenever the controller causes the first rotor and first ultrasonic transducer to move in a given direction along the first linear path, the controller causes the second ultrasonic transducer and the second rotor to be moved in the opposite direction along the second linear path thereby allowing the first and second rotors and the first and second ultrasonic transducers to be subject to at least five G of force when accelerated or decelerated while maintaining the viability of data that is generated when the first and second targets are interrogated.

16. The scanning acoustic microscope of claim 15, wherein the controller is adapted to cause the first and second ultrasonic transducers to emit a pulse of acoustic energy toward each one of a plurality of three-dimensionally varied points located within a given volume defined inside of the first and second targets, respectively, the first and second ultrasonic transducers having, for each one of the pulses, a focal point that is disposed at the same location within the given volume of the first and second targets as the corresponding one of the three dimensionally varied points.

17. The scanning acoustic microscope of claim 15, wherein the controller is adapted to cause the first and second ultrasonic transducers to emit a pulse of acoustic energy toward each one of a plurality of three-dimensionally varied points located within a given volume defined inside of the first and second targets, respectively, the first and second transducers having, for each one of the pulses, a focal point that is disposed at the same location within the given volume of the target as the corresponding one of the three dimensionally varied points inside the first and second targets, respectively, the controller being further adapted to cause the first and second transducers to receive a reflection signal corresponding to each one of the pulses, each one of the reflection signals comprising an A-Scan of the target that is in-focus at the point within the given volume of the first and second targets corresponding thereto, all of the reflection signals representing acoustic impedance features present within the given volume defined inside of the first and second targets.

18. The scanning acoustic microscope of claim 15, wherein the first linear path is co-linear with the second linear path.

19. The scanning acoustic microscope of claim 15, wherein one of the first and second targets comprises a microelectronic target.

20. The scanning acoustic microscope of claim 15, wherein controller is adapted to cause one of the first ultrasonic transducers to be moved in an X-Y raster scan with respect to the first or second target corresponding thereto.

21. The scanning acoustic microscope of claim 15, wherein one of the first and second targets comprises a sealed package.

22. The scanning acoustic microscope of claim 15, wherein one of the first and second targets comprises a biological material.

* * * * *